US011957472B2

(12) United States Patent
Moriya et al.

(10) Patent No.: US 11,957,472 B2
(45) Date of Patent: *Apr. 16, 2024

(54) BRAIN MEASUREMENT APPARATUS AND BRAIN MEASUREMENT METHOD

(71) Applicants: HAMAMATSU PHOTONICS K.K., Hamamatsu (JP); Kyoto University, Kyoto (JP)

(72) Inventors: Takahiro Moriya, Hamamatsu (JP); Takenori Oida, Hamamatsu (JP); Akinori Saito, Hamamatsu (JP); Motohiro Suyama, Hamamatsu (JP); Tetsuo Kobayashi, Kyoto (JP)

(73) Assignees: HAMAMATSU PHOTONICS K.K., Hamamatsu (JP); Kyoto University, Kyoto (JP)

( * ) Notice: Subject to any disclaimer, the term of this patent is extended or adjusted under 35 U.S.C. 154(b) by 389 days.

This patent is subject to a terminal disclaimer.

(21) Appl. No.: 17/346,338

(22) Filed: Jun. 14, 2021

(65) Prior Publication Data

US 2021/0386347 A1    Dec. 16, 2021

(30) Foreign Application Priority Data

Jun. 16, 2020  (JP) ................................ 2020-103953

(51) Int. Cl.
*A61B 5/055* (2006.01)
*A61B 5/00* (2006.01)
(Continued)

(52) U.S. Cl.
CPC .............. *A61B 5/245* (2021.01); *A61B 5/055* (2013.01); *A61B 5/6803* (2013.01);
(Continued)

(58) Field of Classification Search
CPC .. A61B 5/245; A61B 5/0055; G01R 33/0017; G01R 33/26
See application file for complete search history.

(56) References Cited

U.S. PATENT DOCUMENTS 8,305,078 B2   11/2012  Savukov et al.
8,519,705 B2    8/2013  Savukov et al.
(Continued)

FOREIGN PATENT DOCUMENTS

JP    2009-125396 A    6/2009
JP    2011-146621 A    7/2011
(Continued)

OTHER PUBLICATIONS

Velmurugan et al., "Magnetoencephalography recording and analysis" Annals of Indian Academy of Neurology, Mar. 2014; 17(Suppl 1): S113-S119 (Year: 2014).*

(Continued)

*Primary Examiner* — Colin T. Sakamoto
(74) *Attorney, Agent, or Firm* — Faegre Drinker Biddle Reath LLP

(57) ABSTRACT

A brain measurement apparatus includes: a magnetoencephalograph including optically pumped magnetometers, magnetic sensors for measuring geomagnetic field at positions of the optically pumped magnetometers, magnetic sensors for measuring a fluctuating magnetic field at the positions of the optically pumped magnetometers, nulling coils for cancelling the geomagnetic field, and an active shield coil for cancelling the fluctuating magnetic field; an MRI apparatus including nulling coils for applying a static magnetic field and a gradient magnetic field, a transmission coil, and a receive coil; and a control device that, when measuring a brain's magnetic field, controls currents supplied to the nulling coils and the active shield coil based on measured values of the magnetic sensors and, when mea- (Continued)

suring an MR image, controls the static magnetic field and the gradient magnetic field by controlling currents supplied to the nulling coils and generates an MR image from an output of the receive coil.

11 Claims, 4 Drawing Sheets

(51) Int. Cl.
    *A61B 5/245*     (2021.01)
    *G01R 33/00*     (2006.01)
    *G01R 33/26*     (2006.01)
    *G01R 33/34*     (2006.01)
    *G01R 33/421*     (2006.01)
    *G01R 33/54*     (2006.01)

(52) U.S. Cl.
    CPC ......... *G01R 33/0017* (2013.01); *G01R 33/26* (2013.01); *G01R 33/34084* (2013.01); *G01R 33/4215* (2013.01); *G01R 33/543* (2013.01)

(56) References Cited

U.S. PATENT DOCUMENTS

2016/0223622 A1*   8/2016  Yu ..................... G01R 33/0354
2018/0031651 A1*   2/2018  Iaia .................. G01R 33/56563
2020/0072916 A1*   3/2020  Alford ............... G01R 33/0017
2020/0260976 A1*   8/2020  Sasaki .................. A61B 5/4076
2021/0247468 A1*   8/2021  Shapiro ............ G01R 33/56581

FOREIGN PATENT DOCUMENTS

| | | |
|---|---|---|
| JP | 2013-523201 A | 6/2013 |
| JP | 5823195 B2 | 11/2015 |
| JP | 2016-109665 A | 6/2016 |
| WO | WO-2011/117471 A1 | 9/2011 |
| WO | WO-2012/120732 A1 | 9/2012 |

OTHER PUBLICATIONS

Boto, Elena, et al., "Moving magnetoencephalography towards real-world applications with a wearable system," Nature, Mar. 29, 2018, vol. 555.

Iivanainen, Joonas, et al., "On-scalp MEG system utilizing an actively shielded array of optically-pumped magnetometers," NeuroImage Elsevier, 2019, vol. 194, pp. 244-258.

Körber, Rainer, et al., "SQUIDs in biomagnetism: a roadmap towards improved healthcare," Supercond. Sci. Technol. 113001 (30pp), 2016 vol. 29, pp. 1-30.

* cited by examiner

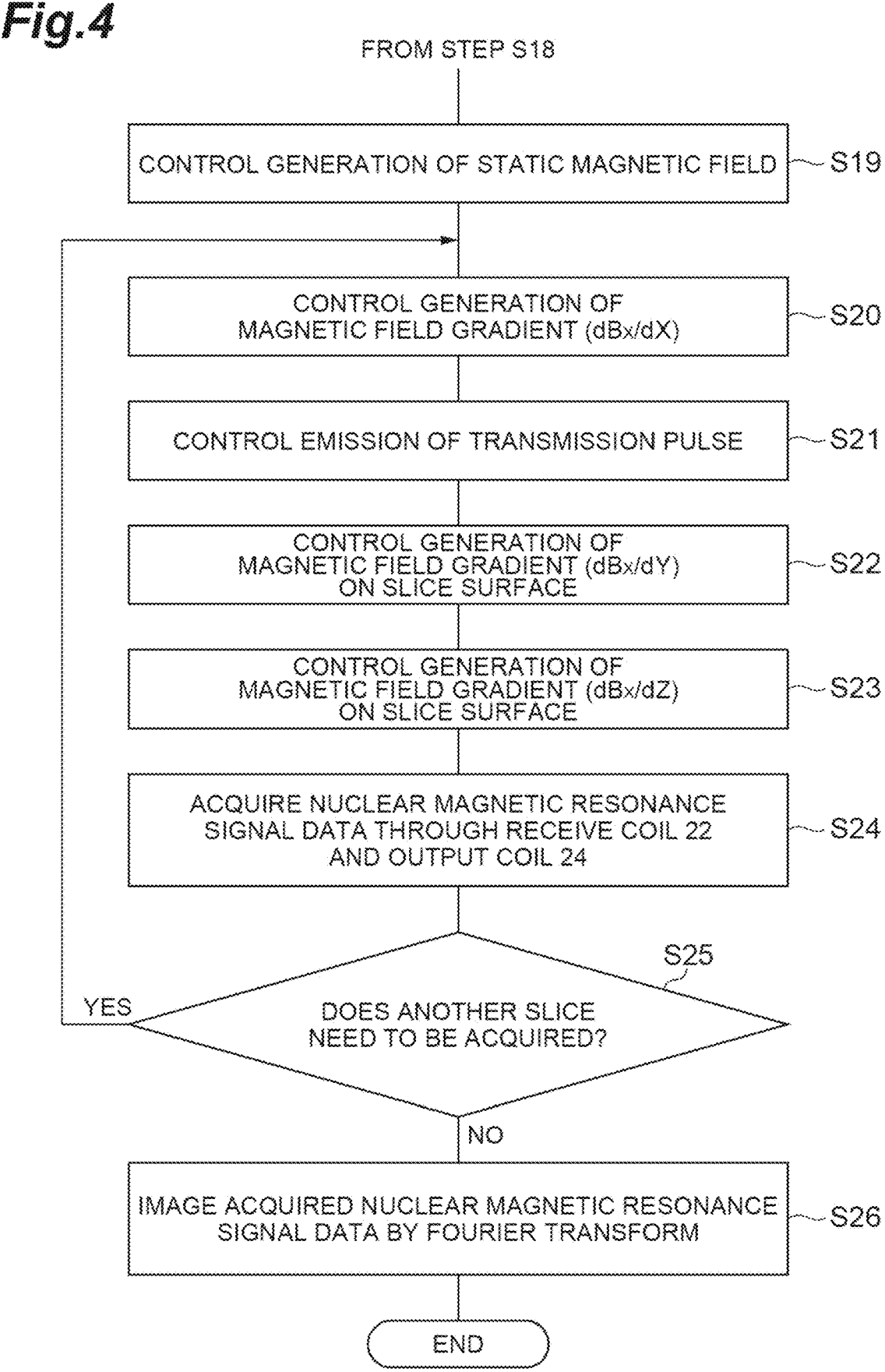

BRAIN MEASUREMENT APPARATUS AND BRAIN MEASUREMENT METHOD

TECHNICAL FIELD

Aspects of the present disclosure relate to a brain measurement apparatus and a brain measurement method.

BACKGROUND

In the related art, as a magnetoencephalograph, a superconducting quantum interference device (SQUID) has been used to measure a small magnetic field of the brain. In recent years, a magnetoencephalograph using an optically pumped magnetometer instead of the SQUID has been studied. The optically pumped magnetometer measures small magnetic fields by detection using the spin polarization of alkali metal atoms excited by optical pumping. For example, Japanese Patent No. 5823195 discloses a magnetoencephalograph using an optical pumping magnetometer. In addition, recently, research has also been conducted to integrate a magnetoencephalograph and a magnetic resonance imaging (MRI) apparatus using the SQUID (see "SQUIDs in biomagnetism: a roadmap towards improved healthcare", Supercond. Sci. Technol. 29 (2016) 113001 (30 pp)).

SUMMARY

Here, the measurement by the magnetoencephalograph needs to be performed in a state in which magnetic noise including the geomagnetic field is reduced, in order to avoid the influence of the magnetic noise stronger than the brain's magnetic field. On the other hand, the measurement by the MRI needs to be performed in a state in which a static magnetic field, a gradient magnetic field, and the like are generated. When trying to realize an apparatus in which a magnetoencephalograph and an MRI apparatus are integrated, it is required to efficiently realize the reduction of magnetic noise and the application of a static magnetic field, a gradient magnetic field, and the like.

The present invention has been made in view of the above circumstances, and it is an object of the present invention to provide a brain measurement apparatus and a brain measurement method capable of efficiently realizing brain's magnetic field measurement and MRI measurement.

A brain measurement apparatus according to one aspect of the present invention includes: a magnetoencephalograph including multiple optically pumped magnetometers configured to measure a brain's magnetic field, multiple magnetic sensors for geomagnetic field cancellation configured to measure a magnetic field relevant to geomagnetic field at a position of each of the multiple optically pumped magnetometers, multiple magnetic sensors for active shield configured to measure a fluctuating magnetic field at the position of each of the multiple optically pumped magnetometers, a geomagnetic field nulling coil for cancelling the magnetic field relevant to the geomagnetic field, and an active shield coil for cancelling the fluctuating magnetic field; an MRI apparatus including a static magnetic field coil for applying a static magnetic field, a gradient magnetic field coil for applying a gradient magnetic field, a transmission coil for transmitting a transmission pulse having a predetermined frequency, and a receive coil for detecting a nuclear magnetic resonance signal generated by the transmission of the transmission pulse; and a controller configured to, when measuring the brain's magnetic field, control a current to be supplied to the geomagnetic field nulling coil and a current to be supplied to the active shield coil based on measured values of the multiple magnetic sensors for geomagnetic field cancellation and measured values of the multiple magnetic sensors for active shield and, when measuring an MR image, control the static magnetic field and the gradient magnetic field by controlling currents to be supplied to the static magnetic field coil and the gradient magnetic field coil and generate an MR image based on an output of the receive coil.

In addition, a brain measurement method according to another aspect of the present invention is a brain measurement method using a magnetoencephalograph including a multiple optically pumped magnetometers configured to measure a brain's magnetic field, multiple magnetic sensors for geomagnetic field cancellation configured to measure a magnetic field relevant to geomagnetic field at a position of each of the multiple optically pumped magnetometers, multiple magnetic sensors for active shield configured to measure a fluctuating magnetic field at the position of each of the multiple optically pumped magnetometers, a geomagnetic field nulling coil for cancelling the magnetic field relevant to the geomagnetic field, and an active shield coil for cancelling the fluctuating magnetic field and an MRI apparatus including a static magnetic field coil for applying a static magnetic field, a gradient magnetic field coil for applying a gradient magnetic field, a transmission coil for transmitting a transmission pulse having a predetermined frequency, and a receive coil for detecting a nuclear magnetic resonance signal generated by the transmission of the transmission pulse. The brain measurement method includes: when measuring the brain's magnetic field, controlling a current to be supplied to the geomagnetic field nulling coil and a current to be supplied to the active shield coil based on measured values of the multiple magnetic sensors for geomagnetic field cancellation and measured values of the multiple magnetic sensors for active shield; and when measuring an MR image, controlling the static magnetic field and the gradient magnetic field by controlling currents to be supplied to the static magnetic field coil and the gradient magnetic field coil and generating an MR image based on an output of the receive coil.

According to the above one aspect or another aspect, the magnetic field relevant to the geomagnetic field and the fluctuating magnetic field at the position of each of the multiple optically pumped magnetometers for measuring the brain's magnetic field are measured. Then, when measuring the brain's magnetic field, the current flowing through the geomagnetic field nulling coil is controlled based on the multiple measured values of the magnetic field relevant to the geomagnetic field, the current flowing through the active shield coil is controlled based on the multiple measured values of the fluctuating magnetic field, and the magnetic field is generated in each of the coils. At the positions of the multiple optically pumped magnetometers, the magnetic field relevant to the geomagnetic field is canceled by the magnetic field generated in the geomagnetic field nulling coil, and the fluctuating magnetic field is canceled by the magnetic field generated in the active shield coil. As a result, since the magnetic field relevant to the geomagnetic field and the fluctuating magnetic field at the positions of the multiple optically pumped magnetometers are canceled, the multiple optically pumped magnetometers can measure the brain's magnetic field in a state in which the influence of the magnetic field relevant to the geomagnetic field and the influence of the fluctuating magnetic field are avoided.

On the other hand, according to the above one aspect or another aspect, when measuring the MR image, the static magnetic field and the gradient magnetic field are applied by controlling the currents flowing through the static magnetic field coil and the gradient magnetic field coil, and the nuclear magnetic resonance signal generated by the transmission of the transmission pulse is detected by the receive coil. As a result, the MR image can be measured based on the output of the receive coil.

According to such a brain measurement apparatus and a brain measurement method, it is possible to efficiently realize brain's magnetic field measurement and MRI measurement using the same apparatus. In particular, in MRI measurement, a superconducting static magnetic field coil is not required, a magnetic shield room for reducing magnetic noise during the measurement of the brain's magnetic field is also not required, and a coolant such as liquid helium required when using the SQUID is also not required. Therefore, it is possible to reduce the size and cost. In addition, since the brain's magnetic field measurement and the MRI measurement can be sequentially performed on the same subject using the same apparatus, it is possible to reduce registration errors in both measurement results.

BRIEF DESCRIPTION OF THE DRAWINGS

FIG. 4 is a flowchart showing the operation of the brain measurement apparatus according to the embodiment.

DETAILED DESCRIPTION

Figure 1:
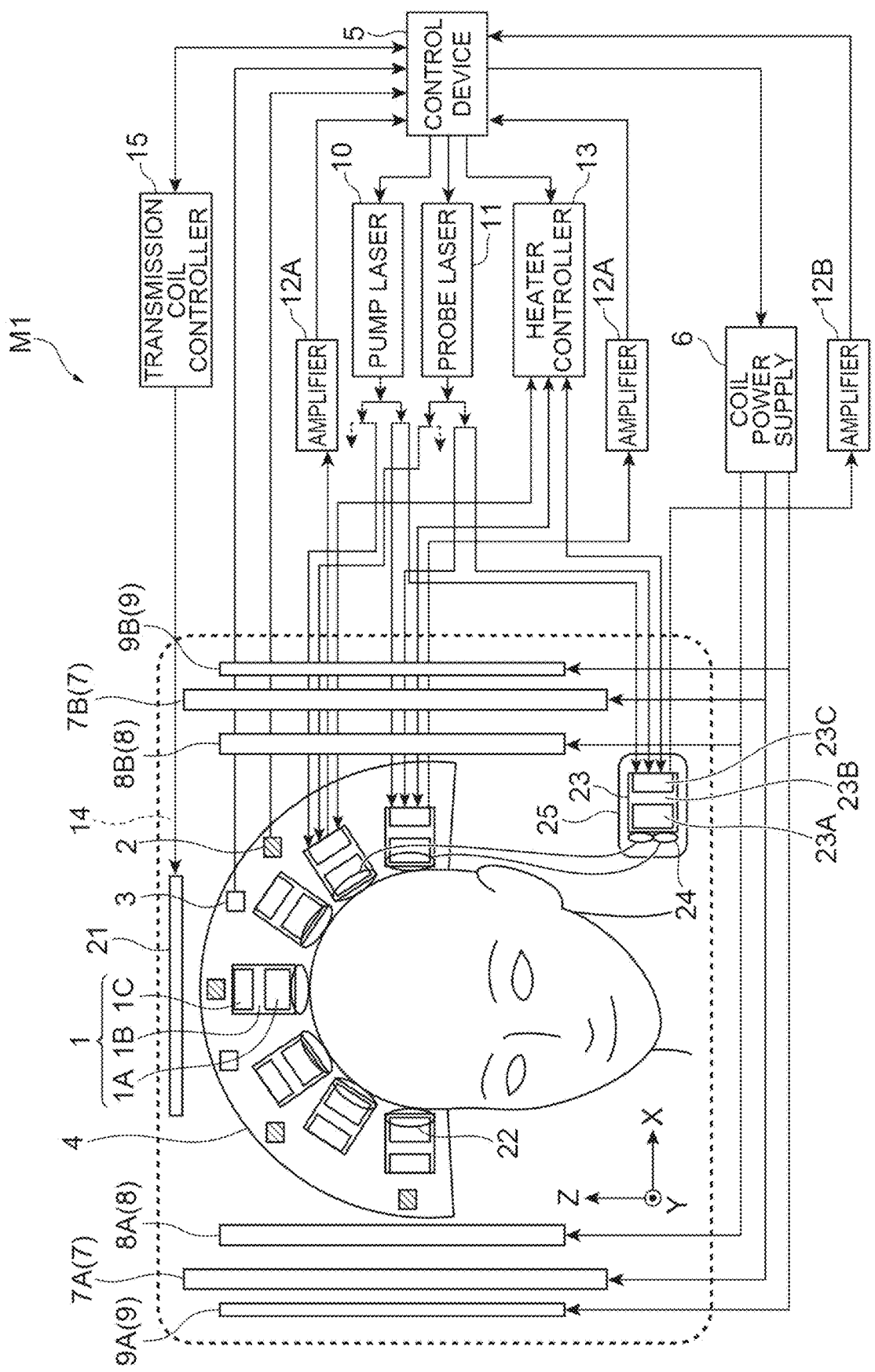
FIG. 1 is a schematic view showing the configuration of a brain measurement apparatus according to an embodiment.

Hereinafter, an embodiment for carrying out the present invention will be described in detail with reference to the accompanying diagrams. In the description of the diagrams, the same elements are denoted by the same reference numerals, and the repeated description thereof will be omitted.

FIG. 1 is a schematic view showing the configuration of a brain measurement apparatus M1 according to an embodiment. The brain measurement apparatus M1 is an apparatus for measuring a brain's magnetic field and a magnetic resonance (MR) image for a subject. The brain measurement apparatus M1 includes: a magnetoencephalograph module having multiple optically pumped magnetometer (OPM) modules 1, multiple magnetic sensors for geomagnetic field cancellation 2, multiple magnetic sensors for active shield 3, a non-magnetic frame 4, a pair of geomagnetic field nulling coils 7, a pair of gradient magnetic field nulling coils 8 (geomagnetic field nulling coils), and a pair of active shield coils 9; and an MRI module having a transmission coil 21, a receive coil 22, an OPM module 23, and an output coil 24. In addition, the brain measurement apparatus M1 includes a control device 5, a coil power supply 6, a pump laser 10, a probe laser 11, amplifiers 12A and 12B, a heater controller 13, an electromagnetic shield 14, and a transmission coil controller 15.

In the following description, a direction approximately parallel to the central axis of the head of the subject is defined as a Z-axis direction and directions perpendicular to the Z axis and perpendicular to each other are defined as an X-axis direction and a Y-axis direction.

Each OPM module 1 includes an optically pumped magnetometer 1A, a heat insulating material 1B, and a read circuit 1C. The multiple OPM modules 1 are arranged at predetermined intervals along the scalp, for example.

The optically pumped magnetometer 1A is a sensor that measures a brain's magnetic field by using optical pumping, and has a sensitivity of, for example, about 10 fT to 10 pT. The heat insulating material 1B prevents heat transfer of the optically pumped magnetometer 1A. The read circuit 1C is a circuit for acquiring the detection result of the optically pumped magnetometer 1A. The pump laser 10 emits pump light to a cell containing alkali metal vapor to excite the alkali metal. The excited alkali metal is in a spin polarization state, and when this receives magnetic field, the inclination of the spin polarization axis of the alkali metal atom changes according to the magnetic field. The inclination of the spin polarization axis is detected by probe light emitted separately from the pump light. In addition, the optically pumped magnetometer 1A is configured such that a predetermined bias magnetic field is applied in the emission direction of the pump light so as to be sensitive to a magnetic field having a frequency included in the range of 0 to 200 Hz. The read circuit 1C receives probe light passing through the alkali metal vapor by a photodiode and acquires the detection result. The read circuit 1C outputs the detection result to the amplifier 12A.

The optically pumped magnetometer 1A may be, for example, an axial gradiometer. The axial gradiometer has a measurement region and a reference region in a direction perpendicular to the scalp (measurement location) of the subject and coaxially. The measurement region is, for example, a location closest to the scalp of the subject among locations where the axial gradiometer measures the brain's magnetic field. The reference region is, for example, a location away from the measurement region by a predetermined distance (for example, 3 cm) in a direction away from the scalp of the subject, among locations where the axial gradiometer measures the brain's magnetic field. The axial gradiometer outputs the respective measurement results in the measurement region and the reference region to the amplifier 12A. Here, when common mode noise is included, its influence is shown in each of the output result of the measurement region and the output result of the reference region. Common mode noise is removed by acquiring the difference between the output result of the measurement region and the output result of the reference region. By removing the common mode noise, the optically pumped magnetometer 1A can obtain a sensitivity of about 10 fT/√Hz, for example, when performing measurement in a magnetic noise environment of 1 pT.

The magnetic sensor for geomagnetic field cancellation 2 is a sensor that measures a magnetic field relevant to the geomagnetic field at a position corresponding to the optically pumped magnetometer 1A, and is, for example, a flux gate sensor having a sensitivity of about 1 nT to 100 μT. The position corresponding to the optically pumped magnetometer 1A is a position around (near) the region where the optically pumped magnetometer 1A is arranged. The magnetic sensor for geomagnetic field cancellation 2 may be provided so as to correspond to the optically pumped magnetometer 1A in a one-to-one manner, or may be provided so as to correspond in a one-to-many manner (one magnetic sensor for geomagnetic field cancellation 2 for multiple optically pumped magnetometers 1A). The magnetic sensor for geomagnetic field cancellation 2 measures, for example, geomagnetic field and a gradient magnetic field of the geomagnetic field (hereinafter, simply referred to as "gradient magnetic field") as magnetic fields relevant to the geomagnetic field, and outputs the measured value to the control device 5. The measured value of the magnetic sensor for geomagnetic field cancellation 2 can be expressed by a vector having a direction and a magnitude. The magnetic sensor for geomagnetic field cancellation 2 may continuously perform measurement and output at predetermined time intervals.

The magnetic sensor for active shield 3 is a sensor that measures a fluctuating magnetic field at a position corresponding to the optically pumped magnetometer 1A, and is, for example, an optically pumped magnetometer having a sensitivity of about 100 fT to 10 nT and different from the optically pumped magnetometer 1A. The position corresponding to the optically pumped magnetometer 1A is a position around (near) the region where the optically pumped magnetometer 1A is arranged. The magnetic sensor for active shield 3 may be provided so as to correspond to the optically pumped magnetometer 1A in a one-to-one manner, or may be provided so as to correspond in a one-to-many manner (one magnetic sensor for active shield 3 for the multiple optically pumped magnetometers 1A). The magnetic sensor for active shield 3 measures a magnetic field of a noise (AC) component of, for example, 200 Hz or less as a fluctuating magnetic field, and outputs the measured value to the control device 5. The measured value of the magnetic sensor for active shield 3 can be expressed by a vector having a direction and a magnitude. The magnetic sensor for active shield 3 may continuously perform measurement and output at predetermined time intervals.

The non-magnetic frame 4 is a frame that covers the entire scalp of the subject whose brain's magnetic field is to be measured, and is formed of a non-magnetic material such as graphite whose relative magnetic permeability is close to 1 and accordingly does not affect the magnetic field distribution. The non-magnetic frame 4 can be, for example, a helmet-type frame that surrounds the entire scalp of the subject and is attached to the head of the subject. The multiple optically pumped magnetometers 1A are fixed to the non-magnetic frame 4 so as to be close to the scalp of the subject. In addition, the magnetic sensor for geomagnetic field cancellation 2 is fixed to the non-magnetic frame 4 so that a magnetic field relevant to the geomagnetic field at the position of each of the multiple optically pumped magnetometers 1A can be measured, and the magnetic sensor for active shield 3 is fixed to the non-magnetic frame 4 so that a fluctuating magnetic field at the position of each of the multiple optically pumped magnetometers 1A can be measured. Since a change in the magnetic field strength according to the position of the fluctuating magnetic field is smaller than that in the case of the static magnetic field, a smaller number of magnetic sensors for active shield 3 than the number of magnetic sensors for geomagnetic field cancellation 2 may be fixed to the non-magnetic frame 4. In addition, the receive coil 22 for detecting a nuclear magnetic resonance signal for MR image measurement is fixed to the scalp side of the subject of the multiple optically pumped magnetometers 1A inside the non-magnetic frame 4. The receive coil 22 detects the nuclear magnetic resonance signal of the proton, which will be described later, and converts the nuclear magnetic resonance signal into an electric current. In order to improve the detection sensitivity of the nuclear magnetic resonance signal, it is preferable that the receive coil 22 is provided on the side of the optically pumped magnetometer 1A close to the scalp of the head of the subject.

The transmission coil 21 is a coil for emitting an RF pulse (transmission pulse) having a predetermined frequency (for example, about 300 kHz) to the head of the subject during MR image measurement. The transmission coil 21 is arranged above the head of the subject outside the non-magnetic frame 4, for example.

The output coil 24 is electrically connected to both ends of the receive coil 22 through a cable, and receives a current flowing through both ends of the receive coil 22, converts the current into a magnetic signal again, and outputs the magnetic signal.

Similar to the OPM module 1, the OPM module 23 includes an optically pumped magnetometer 23A, a heat insulating material 23B, and a read circuit 23C. The OPM module 23 is housed in, for example, a magnetic shield 25 that shields a static magnetic field, which will be described later, outside the non-magnetic frame 4 together with the output coil 24. The magnetic shield 25 is formed of, for example, mu-metal having a relative magnetic permeability of more than 1.

The optically pumped magnetometer 23A is a sensor that measures a magnetic signal using optical pumping. In addition, the optically pumped magnetometer 23A is configured such that a predetermined bias magnetic field is applied in the emission direction of pump light so as to be sensitive to a magnetic field having a frequency included in the range of 20 kHz to 500 kHz. For example, a bias magnetic field of about 40 µT is applied so as to be sensitive to the frequency of 300 kHz of the electromagnetic wave emitted by the proton. The read circuit 23C outputs the detection result of the optically pumped magnetometer 23A to the amplifier 12B.

Figure 2:
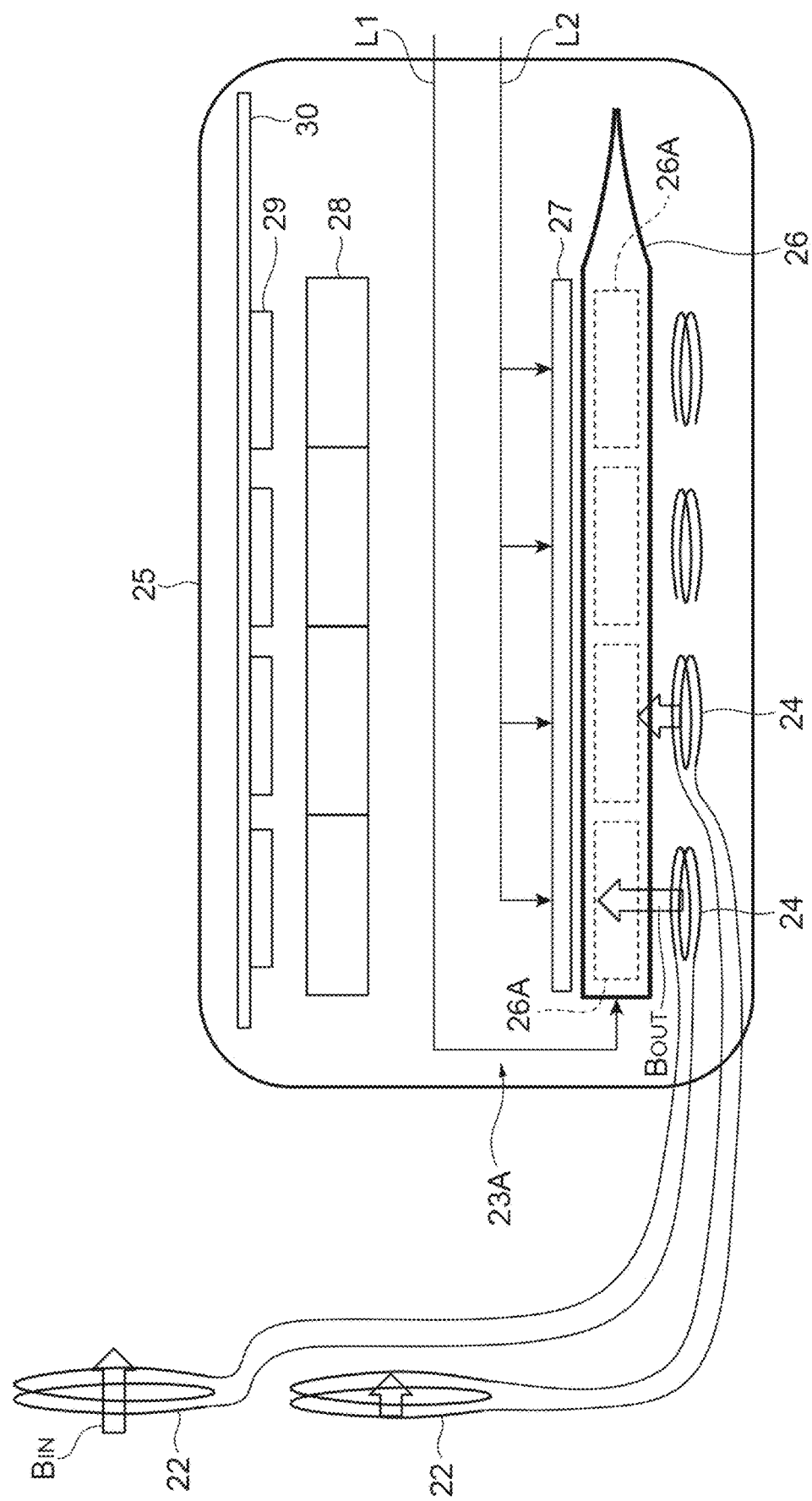
FIG. 2 is a schematic view showing the configuration of an OPM module according to the embodiment.

FIG. 2 shows a specific example of the configuration of the OPM module 23. The optically pumped magnetometer 23A includes a longitudinal cell 26 filled with a gas containing an alkali metal whose direction of polarization changes with a magnetic field to be measured, a heater 27 that heats the entire cell 26 to a predetermined temperature (for example, 180°), a polarization beam splitter 28, and a photodetector 29. Pump light L1 is introduced into the cell 26 from the outside along the longitudinal direction of the inside of the cell 26. In addition, along a direction perpendicular to the longitudinal direction, probe light L2 from the outside is branched and emitted to multiple crossing regions 26A (for example, four crossing regions 26A) divided in the longitudinal direction. The polarization angle of the probe light L2 transmitted through the crossing regions 26A is detected by the polarization beam splitter 28 and the photodetector 29 provided corresponding to each of the crossing regions 26A. That is, the polarization beam splitter 28 separates the probe light L2 into two linearly polarized components perpendicular to each other, and the photodetector 29 detects the intensities of the two linearly polarized components using two built-in photodiodes (PDs) and detects the polarization angle of the probe light L2 based on the ratio of the detected intensities. A circuit board 30 is further provided in the OPM module 23. Through the read circuit 23C in the circuit board 30, the polarization angle of the probe light L2 detected for each crossing region 26A is output.

In the magnetic shield 25, the output coil 24 is fixed so as to face each crossing region 26A of the cell 26 in the OPM module 23 having the above-described configuration. With such a configuration, a magnetic signal $B_{OUT}$ generated by the output coil 24 based on the electromagnetic field $B_{OUT}$ detected by the receive coil 22 is detected based on the polarization angle of the probe light L2 that changes according to the inclination of the spin polarization axis of the alkali metal atom. Here, in the example of FIG. 2, the number of divided crossing regions 26A is four, but may be changed to any number. In addition, multiple cells 26 may be provided in parallel, so that the crossing regions 26A are arrayed in a two-dimensional manner (for example, 4×4=16).

When measuring the brain's magnetic field, the control device 5 determines currents for various coils based on the measured values output from the magnetic sensor for geomagnetic field cancellation 2 and the magnetic sensor for active shield 3, and outputs a control signal for outputting each of the currents to the coil power supply 6. Based on the measured values of the multiple magnetic sensors for geomagnetic field cancellation 2, the control device 5 determines a current for the geomagnetic field nulling coil 7 and the gradient magnetic field nulling coil 8, which are geomagnetic field nulling coils, so as to generate a magnetic field for canceling a magnetic field relevant to the geomagnetic field. In addition, based on the measured values of the multiple magnetic sensors for active shield 3, the control device 5 determines a current for the active shield coil 9 so as to generate a magnetic field for canceling a fluctuating magnetic field. The control device 5 outputs a control signal corresponding to the determined current to the coil power supply 6.

Specifically, the control device 5 determines a current for the geomagnetic field nulling coil 7 so that the average value of the measured values of the multiple magnetic sensors for geomagnetic field cancellation 2 approaches zero (as a result, a magnetic field opposite to the geomagnetic field at the position of the optically pumped magnetometer 1A and having approximately the same magnitude as the geomagnetic field is generated). The control device 5 outputs a control signal (control signal for static magnetic field cancellation) corresponding to the determined current of the geomagnetic field nulling coil 7 to the coil power supply 6.

In addition, the control device 5 determines a current for the gradient magnetic field nulling coil 8 so that the deviation from the average value of the measured values of the multiple magnetic sensors for geomagnetic field cancellation 2 is minimized (as a result, a magnetic field opposite to the gradient magnetic field at the position of the optically pumped magnetometer 1A and having approximately the same magnitude as the gradient magnetic field is generated). The control device 5 outputs a control signal (control signal for static magnetic field cancellation) corresponding to the determined current of the gradient magnetic field nulling coil 8 to the coil power supply 6.

In addition, the control device 5 determines a current for the active shield coil 9 so that the average value of the measured values of the multiple magnetic sensors for active shield 3 approaches zero (as a result, a magnetic field opposite to the fluctuating magnetic field at the position of the optically pumped magnetometer 1A and having approximately the same magnitude as the fluctuating magnetic field is generated). The control device 5 outputs a control signal (control signal for fluctuating magnetic field cancellation) corresponding to the determined current of the active shield coil 9 to the coil power supply 6.

In addition, the control device 5 obtains information regarding the magnetic field detected by the optically pumped magnetometer 1A by using the signal output from the amplifier 12A. When the optically pumped magnetometer 1A is an axial gradiometer, the control device 5 may remove the common mode noise by acquiring the difference between the output result of the measurement region and the output result of the reference region. In addition, the control device 5 may control operations such as the emission timing and the emission time of the pump laser 10 and the probe laser 11.

In addition, when measuring the MR image, the control device 5 determines a current to be supplied to each of the geomagnetic field nulling coil 7 and the gradient magnetic field nulling coil 8, which operate as coils for applying the static magnetic field and the gradient magnetic field, respectively, and outputs a control signal for outputting the current to the coil power supply 6. That is, the control device 5 determines a current flowing through the geomagnetic field nulling coil 7 so that an X-axis direction magnetic field having a predetermined strength (for example, 7 mT) is applied to the head of the subject as a static magnetic field. In addition, the control device 5 selectively determines an X-axis direction magnetic field gradient ($dB_X/dX$), a Y-axis direction magnetic field gradient ($dB_X/dY$), and a Z-axis direction magnetic field gradient ($dB_X/dZ$) as a gradient magnetic field to determine a current flowing through the gradient magnetic field nulling coil 8. Therefore, a slicing position in the MR image can be determined, and the position within the slice surface can be encoded by phase encoding and frequency encoding. In addition, when measuring the MR image, the control device 5 outputs a control signal so that no current is supplied to the active shield coil 9 for removing low-frequency noise.

In addition, when measuring the MR image, the control device 5 outputs a control signal, which is for controlling electric power supplied to the transmission coil 21, to the transmission coil controller 15, so that control to emit a transmission pulse having a predetermined frequency (for example, about 300 kHz when the strength of the static magnetic field is 7 mT) to the head of the subject is performed. As a result, protons on the slice surface (surface selected by the static magnetic field and the gradient magnetic field) resonate to tilt the spin. Thereafter, the control device 5 controls the electric power of the transmission coil 21 to be turned off. As a result, it is possible to acquire the MR image by measuring how the spin returns based on the output of the OPM module 23. More specifically, the control device 5 measures the nuclear magnetic resonance signal from the proton by encoding the position with frequency and phase using a known spin echo sequence or gradient echo sequence, and converts the measurement result into an MR image using FFT.

The control device 5 is physically configured to include a memory such as a RAM and a ROM, a processor (arithmetic circuit) such as a CPU, a communication interface, and a storage unit such as a hard disk. Examples of the control device 5 include a personal computer, a cloud server, a smartphone, and a tablet terminal. The control device 5 functions by executing a program stored in the memory on the CPU of the computer system.

The coil power supply 6 outputs a predetermined current to each of the geomagnetic field nulling coil 7, the gradient magnetic field nulling coil 8, and the active shield coil 9 in response to the control signal output from the control device 5. Specifically, the coil power supply 6 outputs a current to the geomagnetic field nulling coil 7 in response to the control signal relevant to the geomagnetic field nulling coil 7. The coil power supply 6 outputs a current to the gradient magnetic field nulling coil 8 in response to the control signal relevant to the gradient magnetic field nulling coil 8. The coil power supply 6 outputs a current to the active shield coil 9 in response to the control signal relevant to the active shield coil 9.

The transmission coil controller 15 is electrically connected to the transmission coil 21, and supplies electric power to the transmission coil 21 in response to the control signal output from the control device 5 so that a transmission pulse having a predetermined frequency is emitted.

The geomagnetic field nulling coil 7 is a coil for cancelling the magnetic field of the geomagnetic field among the magnetic fields relevant to the geomagnetic field at the position of the optically pumped magnetometer 1A. The geomagnetic field nulling coil 7 generates a magnetic field according to the current supplied from the coil power supply 6 to cancel the geomagnetic field. The geomagnetic field nulling coil 7 has, for example, a pair of geomagnetic field nulling coils 7A and 7B. The pair of geomagnetic field nulling coils 7A and 7B are arranged with the optically pumped magnetometer 1A interposed therebetween (for example, on the left and right of the subject). The pair of geomagnetic field nulling coils 7A and 7B generate a magnetic field, which is opposite to the geomagnetic field at the position of the optically pumped magnetometer 1A and has approximately the same magnitude as the geomagnetic field, according to the current supplied from the coil power supply 6. The direction of the magnetic field is, for example, the X-axis direction, the Y-axis direction, and the Z-axis direction. The geomagnetic field at the position of the optically pumped magnetometer 1A is canceled by a magnetic field generated by the geomagnetic field nulling coil 7, the magnetic field being opposite to the geomagnetic field and having approximately the same magnitude as the geomagnetic field. In this manner, the geomagnetic field nulling coil 7 cancels the geomagnetic field at the position of the optically pumped magnetometer 1A.

In addition, the geomagnetic field nulling coil 7 has a role as a static magnetic field coil for generating a static magnetic field in the X-axis direction during MR image measurement. The geomagnetic field nulling coil 7 generates a static magnetic field having a predetermined strength according to the current supplied from the coil power supply 6.

The gradient magnetic field nulling coil 8 is a coil for cancelling the gradient magnetic field among the magnetic fields relevant to the geomagnetic field at the position of the optically pumped magnetometer 1A. The gradient magnetic field nulling coil 8 generates a magnetic field according to the current supplied from the coil power supply 6 to cancel the gradient magnetic field. The gradient magnetic field nulling coil 8 has, for example, a pair of gradient magnetic field nulling coils 8A and 8B. The pair of gradient magnetic field nulling coils 8A and 8B are arranged with the optically pumped magnetometer 1A interposed therebetween (for example, on the left and right of the subject). The pair of gradient magnetic field nulling coils 8A and 8B generate a magnetic field, which is opposite to the gradient magnetic field at the position of the optically pumped magnetometer 1A and has approximately the same magnitude as the gradient magnetic field, according to the current supplied from the coil power supply 6. The direction of the magnetic field is, for example, the X-axis direction, the Y-axis direction, and the Z-axis direction. The gradient magnetic field at the position of the optically pumped magnetometer 1A is canceled by a magnetic field generated by the gradient magnetic field nulling coil 8, the magnetic field being opposite to the gradient magnetic field and having approximately the same magnitude as the gradient magnetic field. In this manner, the gradient magnetic field nulling coil 8 cancels the gradient magnetic field at the position of the optically pumped magnetometer 1A.

In addition, the gradient magnetic field nulling coil 8 has a role as a gradient magnetic field coil for generating a gradient magnetic field during MR image measurement. The gradient magnetic field nulling coil 8 generates a gradient magnetic field having a selective gradient in the X-axis direction, the Y-axis direction, and the Z-axis direction according to the current supplied from the coil power supply 6.

The active shield coil 9 is a coil for cancelling the fluctuating magnetic field at the position of the optically pumped magnetometer 1A. The active shield coil 9 generates a magnetic field according to the current supplied from the coil power supply 6 to cancel the fluctuating magnetic field. The active shield coil 9 has, for example, a pair of active shield coils 9A and 9B. The pair of active shield coils 9A and 9B are arranged with the optically pumped magnetometer 1A interposed therebetween (for example, on the left and right of the subject). The pair of active shield coils 9A and 9B generate a magnetic field, which is opposite to the fluctuating magnetic field at the position of the optically pumped magnetometer 1A and has approximately the same magnitude as the fluctuating magnetic field, according to the current supplied from the coil power supply 6. The direction of the magnetic field is, for example, the X-axis direction, the Y-axis direction, and the Z-axis direction. The fluctuating magnetic field at the position of the optically pumped magnetometer 1A is canceled by a magnetic field generated by the active shield coil 9, the magnetic field being opposite to the fluctuating magnetic field and having approximately the same magnitude as the fluctuating magnetic field. In this manner, the active shield coil 9 cancels the fluctuating magnetic field at the position of the optically pumped magnetometer 1A.

The pump laser 10 is a laser device that generates pump light. The pump light emitted from the pump laser 10 is incident on each of the multiple optically pumped magnetometers 1A and the optically pumped magnetometers 23A by fiber branching.

The probe laser 11 is a laser device that generates probe light. The probe light emitted from the probe laser 11 is incident on each of the multiple optically pumped magnetometers 1A and the optically pumped magnetometers 23A by fiber branching.

The amplifier 12A is a device or circuit that amplifies an output result signal from the OPM module 1 (specifically, the read circuit 1C) and outputs the signal to the control device 5.

The amplifier 12B is a device or circuit that amplifies an output result signal from the OPM module 23 (specifically, the read circuit 23C) and outputs the signal to the control device 5.

The heater controller 13 is a temperature adjusting device connected to a heater for heating the cell of the optically pumped magnetometer 1A and the cell of the optically pumped magnetometer 23A and a thermocouple (not shown) for measuring the temperature of each cell. The heater controller 13 adjusts the temperature of each cell by receiving the temperature information of the cell from the thermocouple and adjusting the heating of the heater based on the temperature information.

The electromagnetic shield 14 is a shield member for shielding high-frequency (for example, 10 kHz or higher) electromagnetic noise. For example, the electromagnetic shield 14 is formed of a mesh woven with metal threads, a non-magnetic metal plate such as aluminum, or the like. The electromagnetic shield 14 is arranged so as to surround the OPM modules 1 and 23, the transmission coil 21, the receive coil 22, the output coil 24, the magnetic sensor for geomagnetic field cancellation 2, the magnetic sensor for active shield 3, the non-magnetic frame 4, the geomagnetic field nulling coil 7, the gradient magnetic field nulling coil 8, and the active shield coil 9. The electromagnetic shield 14 can prevent noise in the 300 kHz band, which is a measurement frequency, from entering the receive coil 22 to increase the noise during MR image measurement. In addition, it is possible to prevent high-frequency noise from entering the optically pumped magnetometer 1A to cause an unstable operation during the measurement of the brain's magnetic field.

Figure 3:
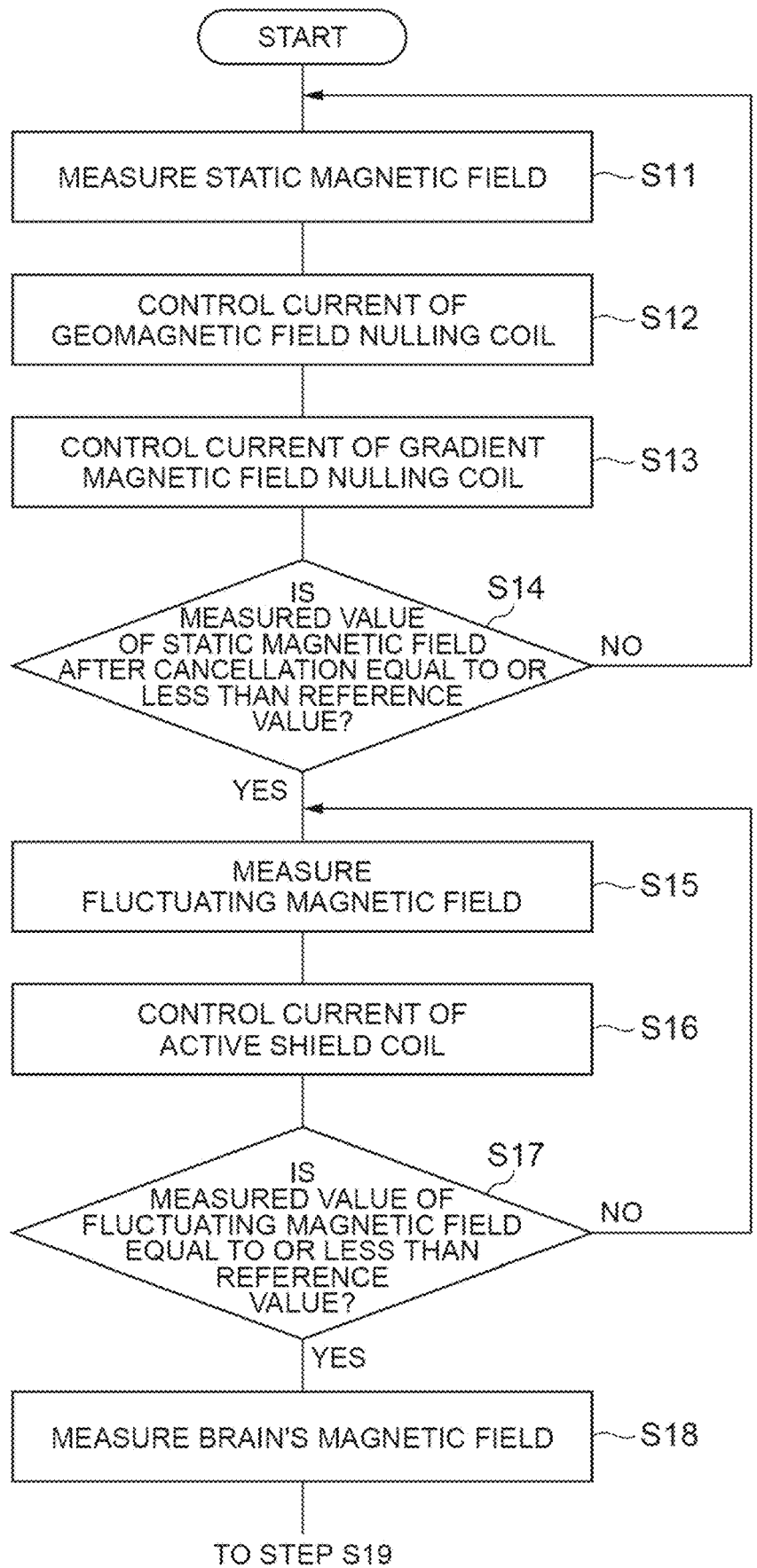
FIG. 3 is a flowchart showing the operation of the brain measurement apparatus according to the embodiment.

Next, a brain measurement method using the brain measurement apparatus M1 according to the embodiment will be described with reference to FIGS. 3 and 4. FIGS. 3 and 4 are flowcharts showing the operation of the brain measurement apparatus M1.

First, when the measurement of the brain's magnetic field starts with the non-magnetic frame 4 attached to the subject, the magnetic sensor for geomagnetic field cancellation 2 measures a magnetic field relevant to the geomagnetic field, which is a static magnetic field (step S11). The magnetic sensor for geomagnetic field cancellation 2 measures the geomagnetic field and the gradient magnetic field at each position of the optically pumped magnetometer 1A, and outputs the measured values to the control device 5.

The control device 5 and the coil power supply 6 control a current for the geomagnetic field nulling coil 7 (step S12). The control device 5 determines a current for the geomagnetic field nulling coil 7 based on the measured value of the magnetic sensor for geomagnetic field cancellation 2 so that a magnetic field opposite to the geomagnetic field at the position of the optically pumped magnetometer 1A and having approximately the same magnitude as the geomagnetic field is generated. More specifically, the control device 5 determines a current for the geomagnetic field nulling coil 7 so that the average value of the measured values of the multiple magnetic sensors for geomagnetic field cancellation 2 approaches zero, for example. The control device 5 outputs a control signal corresponding to the determined current to the coil power supply 6. The coil power supply 6 outputs a predetermined current to the geomagnetic field nulling coil 7 in response to the control signal output from the control device 5. The geomagnetic field nulling coil 7 generates a magnetic field according to the current supplied from the coil power supply 6. The geomagnetic field at the position of the optically pumped magnetometer 1A is canceled by a magnetic field generated by the geomagnetic field nulling coil 7, the magnetic field being opposite to the geomagnetic field and having approximately the same magnitude as the geomagnetic field.

The control device 5 and the coil power supply 6 control a current for the gradient magnetic field nulling coil 8 (step S13). The control device 5 determines a current for the gradient magnetic field nulling coil 8 based on the measured value of the magnetic sensor for geomagnetic field cancellation 2 so that a magnetic field opposite to the gradient magnetic field at the position of the optically pumped magnetometer 1A and having approximately the same magnitude as the gradient magnetic field is generated. More specifically, the control device 5 determines a current for the gradient magnetic field nulling coil 8 so that the deviation from the average value of the measured values of the multiple magnetic sensors for geomagnetic field cancellation 2 is minimized, for example. The control device 5 outputs a control signal corresponding to the determined current to the coil power supply 6. The coil power supply 6 outputs a predetermined current to the gradient magnetic field nulling coil 8 in response to the control signal output from the control device 5. The gradient magnetic field nulling coil 8 generates a magnetic field according to the current supplied from the coil power supply 6. The gradient magnetic field at the position of the optically pumped magnetometer 1A is canceled by a magnetic field generated by the gradient magnetic field nulling coil 8, the magnetic field being opposite to the gradient magnetic field and having approximately the same magnitude as the gradient magnetic field.

The control device 5 determines whether or not the measured value of the static magnetic field (magnetic field relevant to the geomagnetic field) after the cancellation is equal to or less than the reference value (step S14). The measured value of the static magnetic field after the cancellation is a value measured by the magnetic sensors for geomagnetic field cancellation 2 after the static magnetic field is canceled by the geomagnetic field nulling coil 7 and the gradient magnetic field nulling coil 8. The reference value is the magnitude of the magnetic field in which the optically pumped magnetometer 1A normally operates, and can be set to, for example, 1 nT. If the measured value of the static magnetic field is not equal to or less than the reference value ("NO" in step S14), the process returns to step S11. If the measured value of the static magnetic field is equal to or less than the reference value ("YES" in step S14), the process proceeds to step S15.

The magnetic sensor for active shield 3 measures a fluctuating magnetic field (step S15). The magnetic sensor for active shield 3 measures a fluctuating magnetic field at each position of the optically pumped magnetometer 1A and outputs the measured value to the control device 5.

The control device 5 and the coil power supply 6 control a current for the active shield coil 9 (step S16). The control device 5 determines a current for the active shield coil 9 based on the measured value of the magnetic sensor for active shield 3 so that a magnetic field opposite to the fluctuating magnetic field at the position of the optically pumped magnetometer 1A and having approximately the same magnitude as the fluctuating magnetic field is generated. More specifically, the control device 5 determines a current for the active shield coil 9 so that the average value of the measured values of the multiple magnetic sensors for active shield 3 approaches zero, for example. The control device 5 outputs a control signal corresponding to the determined current to the coil power supply 6. The coil power supply 6 outputs a predetermined current to the active shield coil 9 in response to the control signal output from the control device 5. The active shield coil 9 generates a magnetic field according to the current supplied from the coil power supply 6. The fluctuating magnetic field at the position of the optically pumped magnetometer 1A is canceled by a magnetic field generated by the active shield coil 9, the magnetic field being opposite to the fluctuating magnetic field and having approximately the same magnitude as the fluctuating magnetic field.

The control device 5 determines whether or not the measured value of the fluctuating magnetic field after the cancellation is equal to or less than the reference value (step S17). The measured value of the fluctuating magnetic field after the cancellation is a value measured by the magnetic sensor for active shield 3 after the fluctuating magnetic field is canceled by the active shield coil 9. The reference value is a noise level at which the brain's magnetic field can be measured, and can be set to, for example, 1 pT. If the measured value of the fluctuating magnetic field is not less than or equal to the reference value ("NO" in step S17), the process returns to step S15. If the measured value of the fluctuating magnetic field is equal to or less than the reference value ("YES" in step S17), the process proceeds to step S18.

The optically pumped magnetometer 1A measures a brain's magnetic field (step S18). The control device 5 outputs the acquired measurement result to a predetermined output destination. The predetermined output destination may be a memory of the control device 5, a storage device of the control device 5 such as a hard disk, an output device of the control device 5 such as a display, or an external device such as a terminal device connected through a communication interface. Since the static magnetic field (magnetic field relevant to the geomagnetic field) and the fluctuating magnetic field at the position of the optically pumped magnetometer 1A are canceled so as to be equal to or less than a predetermined reference value, the optically pumped magnetometer 1A can measure the brain's magnetic field in a state in which the influence of the static magnetic field (magnetic field relevant to the geomagnetic field) and the influence of the fluctuating magnetic field are avoided.

Moving to FIG. 4, when MR image measurement starts subsequently with the non-magnetic frame 4 attached to the subject, the control device 5 controls the generation of a static magnetic field in the X-axis direction in the head of the subject by determining a current to be supplied to the geomagnetic field nulling coil 7 for applying the static magnetic field and outputting a control signal to the coil power supply 6 (step S19). Then, the control device 5 controls the generation of an X-axis direction magnetic field gradient ($dB_X/dX$) by determining a current to be supplied to the gradient magnetic field nulling coil 8 for generating the gradient magnetic field and outputting a control signal to the coil power supply 6 (step S20). At the same time, the control device 5 outputs a control signal, which is for controlling the electric power to be supplied to the transmission coil 21, to the transmission coil controller 15 to control the transmission pulse to be emitted to the head of the subject (step S21). As a result, protons on a predetermined slice surface are excited.

In addition, the control device 5 controls the generation of a Y-axis direction magnetic field gradient ($dB_X/dY$) on the slice surface by determining a current to be supplied to the gradient magnetic field nulling coil 8 for generating the gradient magnetic field and outputting a control signal to the coil power supply 6 (step S22). As a result, phase encoding is performed. Then, the control device 5 controls the generation of a Z-axis direction magnetic field gradient ($dB_X/dZ$) on the slice surface by determining a current to be supplied to the gradient magnetic field nulling coil 8 for generating the gradient magnetic field and outputting a control signal to the coil power supply 6 (step S23). As a result, frequency encoding is performed.

At the same time, a nuclear magnetic resonance signal from the proton is output from the OPM module 23 through the receive coil 22 and the output coil 24, and the control device 5 acquires the data of the nuclear magnetic resonance signal (step S24). Thereafter, the control device 5 determines whether or not to acquire nuclear magnetic resonance signal data regarding another slice surface (step S25). As a result of the determination, when nuclear magnetic resonance signal data regarding another slice surface is acquired ("YES" in step S25), the process returns to step S20. On the other hand, when nuclear magnetic resonance signal data regarding another slice surface is not acquired ("NO" in step S25), an MR image is acquired by Fourier-transforming the nuclear magnetic resonance signal data acquired so far (step S26). The control device 5 outputs the acquired MR image to a predetermined output destination. The predetermined output destination may be a memory of the control device 5, a storage device of the control device 5 such as a hard disk, an output device of the control device 5 such as a display, or an external device such as a terminal device connected through a communication interface.

[Operational Effects]

Next, the operational effects of the brain measurement apparatus according to the above embodiment will be described.

According to the brain measurement apparatus M1 according to the present embodiment, the magnetic field relevant to the geomagnetic field and the fluctuating magnetic field at the position of each of the multiple optically pumped magnetometers 1A for measuring the brain's magnetic field are measured. Then, when measuring the brain's magnetic field, the current flowing through the geomagnetic field nulling coil 7 and the gradient magnetic field nulling coil 8 is controlled based on the multiple measured values of the magnetic field relevant to the geomagnetic field, the current flowing through the active shield coil 9 is controlled based on the multiple measured values of the fluctuating magnetic field, and the magnetic fields are generated in the respective coils 7, 8, and 9. At the positions of the multiple optically pumped magnetometers 1A, the magnetic field relevant to the geomagnetic field is canceled by the magnetic fields generated by the geomagnetic field nulling coil 7 and the gradient magnetic field nulling coil 8, and the fluctuating magnetic field is canceled by the magnetic field generated in the active shield coil 9. As a result, since the magnetic field relevant to the geomagnetic field and the fluctuating magnetic field at the positions of the multiple optically pumped magnetometers 1A are canceled, the multiple optically pumped magnetometers 1A can measure the brain's magnetic field in a state in which the influence of the magnetic field relevant to the geomagnetic field and the influence of the fluctuating magnetic field are avoided.

On the other hand, according to the embodiment described above, when measuring the MR image, the static magnetic field and the gradient magnetic field are applied by controlling the currents flowing through the geomagnetic field nulling coil 7 and the gradient magnetic field nulling coil 8, and the nuclear magnetic resonance signal generated by the transmission of the transmission pulse is detected by the receive coil 22. As a result, the MR image can be measured based on the output of the receive coil 22.

According to such a brain measurement apparatus and a brain measurement method, it is possible to efficiently realize brain's magnetic field measurement and MRI measurement using the same apparatus. In particular, in MRI measurement, since an optically pumped magnetometer is used, a frequency band having a higher sensitivity than the SQUID can be widely adjusted, so that the strength of the applied static magnetic field, that is, the resonance frequency of protons is less limited. A prepolarized coil that has been required since the SQUID operates only at the low resonance frequency, that is, in the low static magnetic field, is not required, and a coolant such as liquid helium required when using the SQUID is also not required. In addition, since the frequency of the signal measured by MRI is also relatively high, a magnetic shield room for reducing magnetic noise during MRI measurement and brain's magnetic field measurement is also not required. As a result, it is possible to reduce the size and cost of the apparatus. In addition, since the time required for prepolarization is approximately the same as the measurement time, the measurement time can also be shortened to ½ in the present embodiment.

In addition, in the present embodiment, since the static magnetic field can be easily turned on and off by turning on and off the current flowing through the geomagnetic field nulling coil 7, it is possible to perform switching between the brain's magnetic field measurement and the MRI measurement in a short time. Therefore, since the brain's magnetic field measurement and the MRI measurement can be sequentially performed on the same subject using the same apparatus, it is possible to reduce registration errors in both measurement results.

As described above, according to the present embodiment, since the MRI measurement can be performed in a low magnetic field, a special room is not required and the T1 contrast can also be increased. In addition, since the active shield coil 9 is used, it is not necessary to measure the brain's magnetic field in the magnetic shield room. Therefore, since the brain's magnetic field measurement and the MRI measurement can be realized by the same apparatus, both measurements can be sequentially performed while the subject is sitting on a chair or the like. In addition, since the cost of the apparatus can be reduced, the above described measurements can also be performed with the subject on a vehicle or the like. As a result, it is possible to contribute to the diagnosis of mental illness, such as depression and schizophrenia, and neurodegenerative diseases, such as dementia.

Here, the brain measurement apparatus M1 uses the geomagnetic field nulling coil 7 for applying a static magnetic field and the gradient magnetic field nulling coil 8 for applying a gradient magnetic field. Therefore, since a coil for geomagnetic field cancellation for brain's magnetic field measurement and a coil for MRI measurement can be shared, it is possible to further reduce the size and cost of the apparatus.

In addition, in the present embodiment, the magnetic field relevant to the geomagnetic field and the fluctuating magnetic field at the positions of the multiple optically pumped magnetometers 1A are canceled at the time of brain's magnetic field measurement, so that the multiple optically pumped magnetometers 1A can measure the brain's magnetic field in a state in which the influence of the magnetic field relevant to the geomagnetic field and the influence of the fluctuating magnetic field are reliably avoided. As a result, the brain's magnetic field can be measured with high accuracy without using the magnetic shield room. Such an operation can be realized even if the head of the subject moves.

In addition, each of the geomagnetic field nulling coil 7, the gradient magnetic field nulling coil 8, and the active shield coil 9 is formed by a pair of coils arranged with multiple optically pumped magnetometers 1A interposed therebetween. According to such a configuration, the magnetic field relevant to the geomagnetic field and the fluctuating magnetic field at the positions of the multiple optically pumped magnetometers 1A interposed between the pair of coils are effectively canceled. In this manner, the magnetic field relevant to the geomagnetic field and the fluctuating magnetic field can be appropriately canceled by a simple configuration.

In addition, the brain measurement apparatus M1 further includes the output coil 24 electrically connected to the receive coil 22 through a cable and another optically pumped magnetometer 23A for detecting the magnetic signal output by the output coil 24. According to such a configuration, it is possible to avoid the influence of the static magnetic field applied at the time of MRI measurement on the detection signal in another optically pumped magnetometer 23A, so that the accuracy of MR image measurement can be improved. That is, for example, the frequency of the nuclear magnetic resonance signal generated by protons when a static magnetic field of 7 mT is applied is about 300 kHz, and it is necessary to apply a bias magnetic field of about 40 µT in order to give sensitivity to this frequency in the optically pumped magnetometer 23A. When the optically pumped magnetometer 23A is arranged near the head of the subject, it is difficult to achieve both such a bias magnetic field and a static magnetic field. In the present embodiment, since the receive coil 22 having no sensitivity to the static magnetic field can be arranged near the head and the optically pumped magnetometer 23A can be arranged away from the head, it is possible to detect the nuclear magnetic resonance signal with high sensitivity.

In addition, the multiple optically pumped magnetometers 1A are axial gradiometers having a measurement region and a reference region in a direction perpendicular to the scalp of the subject and coaxially. According to such a configuration, since the influence of common mode noise is shown in each of the output result of the measurement region and the output result of the reference region, the common mode noise can be removed by acquiring the difference between the output results of both. As a result, the measurement accuracy of the brain's magnetic field is improved.

In addition, the multiple optically pumped magnetometers 1A, the multiple magnetic sensors for geomagnetic field cancellation 2, the multiple magnetic sensors for active shield 3, and the receive coil 22 are fixed to the helmet-type non-magnetic frame 4 attached to the head of the subject. According to such a configuration, the non-magnetic frame 4 attached to the head and the sensors 2 and 3 and the receive coil 22 fixed to the non-magnetic frame 4 move according to the movement of the head of the subject. Therefore, even when the head of the subject moves, it is possible to appropriately cancel the magnetic field relevant to the geomagnetic field and the fluctuating magnetic field at the positions of the multiple optically pumped magnetometers 1A, measure the brain's magnetic field, and perform MRI measurement. As a result, it is possible to suppress registration errors in both measurements.

In addition, the electromagnetic shield 14 for shielding high-frequency electromagnetic noise may be further provided. According to such a configuration, it is possible to prevent high-frequency electromagnetic noise, which is not a measurement target of the magnetoencephalograph, from entering the multiple optically pumped magnetometers 1A. As a result, the measurement of the brain's magnetic field by the multiple optically pumped magnetometers 1A can be stably performed. At the same time, it is possible to prevent noise in the 300 kHz band, which is the measurement frequency of MRI, from entering the receive coil 22 to increase the noise in the MRI measurement.

In addition, the multiple optically pumped magnetometers 1A are configured to be applied a bias magnetic field so as to be sensitive to frequencies included in the range of 0 to 200 Hz, and another optically pumped magnetometer 23A is configured to be applied a bias magnetic field so as to be sensitive to frequencies included in the range of 20 kHz to 500 kHz. With such a configuration, the measurement sensitivity of the brain's magnetic field can be increased, and at the same time, the accuracy of the MRI measurement can also be improved.

Modification Examples

The above description has been made in detail based on the embodiment of the present disclosure. However, the present disclosure is not limited to the embodiment described above. The present disclosure can be modified in various ways without departing from its gist.

Although the active shield coil 9 has been described as having a pair of active shield coils 9A and 9B, the active shield coil 9 may be arranged as a three-coil system for each OPM module 1 (optically pumped magnetometer 1A). In this case, the control device 5 determines a current for the active shield coil 9 so that a magnetic field opposite to the components of the fluctuating magnetic field in the three directions (x axis, y axis, and z axis) at the position of the optically pumped magnetometer 1A and having approximately the same magnitude as the components of the fluctuating magnetic field is generated. The control device 5 outputs a control signal corresponding to the determined current relevant to each of the active shield coils 9, which are arranged as a three-coil system, to the coil power supply 6. According to such a configuration, the power consumption for cancelling the fluctuating magnetic field can be made relatively small.

In addition, when measuring the MR image, the control device 5 may set the current flowing through the gradient magnetic field nulling coil 8 so as to cancel the gradient magnetic field relevant to the geomagnetic field, or may set the current flowing through the gradient magnetic field nulling coil 8 so as not to cancel the gradient magnetic field relevant to the geomagnetic field. Since the magnitude of the gradient magnetic field is about several µT and is about two orders of magnitude lower than that of the static magnetic field, high accuracy can be maintained without cancellation when acquiring the MR image.

In addition, the brain measurement apparatus M1 of the embodiment described above may not include the optically pumped magnetometer 23A, or may have a configuration in which the control device 5 directly detects the output from the receive coil 22 through the amplifier.

In addition, the optically pumped magnetometer 1A is not limited to the pump & probe type that uses pump light and probe light, and may be a zero field type optically pumped magnetometer that uses circularly polarized light that also serves as pump light and probe light. In this zero field type, light can be emitted to the cell and a periodic bias magnetic field can be applied to the cell for the lock-in detection of the magnetic field, and the deviation from the zero magnetic field can be measured as the brain's magnetic field.

In addition, in the brain measurement apparatus M1 of the embodiment described above, the position of the non-magnetic frame 4 may be optically measurable. For example, a marker attached to the periphery of the lower end of the non-magnetic frame 4 at intervals of 120° and a camera facing the non-magnetic frame 4 may be provided so that the position variation of the helmet can be measured by using the camera. This measurement result can be used at the time of MRI measurement. For example, the control device 5 can calibrate the MR image by calculating the relative position between the gradient magnetic field nulling coil 8 and the receive coil 22 using the measurement result. As a result, a high-resolution MR image can be acquired even if the head of the subject moves. This is a useful configuration for MRI measurement of a subject whose head is difficult to fix, such as an infant. In addition, at the time of brain's magnetic field measurement, even if the position of the head is displaced, the magnetic field at the position of the optically pumped magnetometer 1A in the displaced state is canceled so as to be zero. Therefore, the need to measure the position of the non-magnetic frame 4 is low, but the position information of the non-magnetic frame 4 may be used to generate a zero magnetic field.

In the embodiment described above, it is preferable that the static magnetic field coil is formed by a geomagnetic field nulling coil for cancelling the magnetic field of the geomagnetic field and a gradient magnetic field nulling coil for cancelling the gradient magnetic field of the geomagnetic field. In such a configuration, since the geomagnetic field nulling coil and the static magnetic field coil can be shared, and the gradient magnetic field nulling coil and the gradient magnetic field coil can be shared, it is possible to further reduce the size and cost of the apparatus.

In addition, it is also preferable that the controller determines a current to be supplied to the geomagnetic field nulling coil so as to generate a magnetic field for canceling the magnetic field relevant to the geomagnetic field and determines a current to be supplied to the active shield coil so as to generate a magnetic field for canceling the fluctuating magnetic field. According to such a configuration, since the magnetic field relevant to the geomagnetic field and the fluctuating magnetic field at the positions of the multiple optically pumped magnetometers are canceled, the multiple optically pumped magnetometers can measure the brain's magnetic field in a state in which the influence of the magnetic field relevant to the geomagnetic field and the influence of the fluctuating magnetic field are reliably avoided. As a result, the brain's magnetic field can be measured with high accuracy without using the magnetic shield room.

In addition, it is also preferable that each of the geomagnetic field nulling coil and the active shield coil is a pair of coils arranged with multiple optically pumped magnetometers interposed therebetween. According to such a configuration, the magnetic field relevant to the geomagnetic field and the fluctuating magnetic field at the positions of the multiple optically pumped magnetometers interposed between the pair of geomagnetic field nulling coils and between the pair of active shield coils are effectively canceled. In this manner, the magnetic field relevant to the geomagnetic field and the fluctuating magnetic field can be appropriately canceled by a simple configuration.

In addition, it is also preferable to further include an output coil, which is electrically connected to the receive coil and is configured to output a magnetic signal based on the current flowing through the receive coil, and another optically pumped magnetometer configured to detect the magnetic signal output by the output coil, and it is preferable that the controller generates an MR image based on the magnetic signal detected by another optically pumped magnetometer. According to such a configuration, since the signal can be received by another optically pumped magnetometer having a high sensitivity of fT or more, the accuracy of MR image measurement can be improved. In addition, since another optically pumped magnetometer is arranged at a position away from the receive coil to which a static magnetic field of approximately mT is applied, it is possible to adjust the sensitivity band of the sensor without being affected by the static magnetic field.

In addition, it is also preferable that the multiple optically pumped magnetometers are axial gradiometers having a measurement region and a reference region in a direction perpendicular to the scalp of the subject and coaxially. According to such a configuration, since the influence of common mode noise is shown in each of the output result of the measurement region and the output result of the reference region, the common mode noise can be removed by acquiring the difference between the output results of both. As a result, the measurement accuracy of the brain's magnetic field is improved.

In addition, it is also preferable that the multiple optically pumped magnetometers, the multiple magnetic sensors for geomagnetic field cancellation, the multiple magnetic sensors for active shield, and the receive coil are fixed to the non-magnetic frame which is a helmet-type frame attached to the head of the subject and whose relative magnetic permeability is close to 1 and accordingly does not affect the magnetic field distribution. According to such a configuration, the non-magnetic frame attached to the head and each sensor and the receive coil fixed to the non-magnetic frame move according to the movement of the head of the subject. Therefore, even when the head of the subject moves, it is possible to appropriately cancel the magnetic field relevant to the geomagnetic field and the fluctuating magnetic field at the positions of the multiple optically pumped magnetometers, measure the brain's magnetic field, and perform MRI measurement. As a result, it is possible to suppress registration errors in both measurements.

In addition, an electromagnetic shield for shielding high-frequency electromagnetic noise may be further provided. According to such a configuration, it is possible to prevent high-frequency electromagnetic noise, which cannot be measured by the magnetoencephalograph, from entering the multiple optically pumped magnetometers. As a result, the measurement of the brain's magnetic field by the multiple optically pumped magnetometers can be stably performed. On the other hand, in the MRI measurement, it is possible to prevent the intrusion of noise in the 20 kHz to 500 kHz band, which is a signal region.

In addition, it is also preferable that the multiple optically pumped magnetometers are configured to be applied a bias magnetic field so as to be sensitive to frequencies included in the range of 0 to 200 Hz, and another optically pumped magnetometer is configured to be applied a bias magnetic field so as to be sensitive to frequencies included in the range of 20 kHz to 500 kHz. With such a configuration, the measurement sensitivity of the brain's magnetic field can be increased, and at the same time, the accuracy of the MRI measurement can also be improved.

What is claimed is:

1. A brain measurement apparatus, comprising:
a magnetoencephalograph including multiple optically pumped magnetometers configured to measure a brain's magnetic field, multiple magnetic sensors for geomagnetic field cancellation configured to measure a magnetic field relevant to geomagnetic field at a position of each of the multiple optically pumped magnetometers, multiple magnetic sensors for active shield configured to measure a fluctuating magnetic field at the position of each of the multiple optically pumped magnetometers, a geomagnetic field nulling coil for cancelling the magnetic field relevant to the geomagnetic field, and an active shield coil for cancelling the fluctuating magnetic field;
an MRI apparatus including a static magnetic field coil for applying a static magnetic field, a gradient magnetic field coil for applying a gradient magnetic field, a transmission coil for transmitting a transmission pulse having a predetermined frequency, and a receive coil for detecting a nuclear magnetic resonance signal generated by the transmission of the transmission pulse;
a controller configured to, when measuring the brain's magnetic field, control a current to be supplied to the geomagnetic field nulling coil and a current to be supplied to the active shield coil based on measured values of the multiple magnetic sensors for geomagnetic field cancellation and measured values of the multiple magnetic sensors for active shield and, when measuring an MR image, control the static magnetic field and the gradient magnetic field by controlling currents to be supplied to the static magnetic field coil and the gradient magnetic field coil and generate an MR image based on an output of the receive coil;
an output coil that is electrically connected to the receive coil and is configured to output a magnetic signal based on a current flowing through the receive coil; and
another optically pumped magnetometer configured to detect the magnetic signal output by the output coil,
wherein the controller generates the MR image based on the magnetic signal detected by the another optically pumped magnetometer.

2. The brain measurement apparatus according to claim 1, wherein the geomagnetic field nulling coil is formed by a geomagnetic field nulling coil for cancelling a magnetic field of the geomagnetic field and a gradient magnetic field nulling coil for cancelling a gradient magnetic field of the geomagnetic field.

3. The brain measurement apparatus according to claim 1, wherein the controller determines a current to be supplied to the geomagnetic field nulling coil so as to generate a magnetic field for canceling the magnetic field relevant to the geomagnetic field, and determines a current to be supplied to the active shield coil so as to generate a magnetic field for canceling the fluctuating magnetic field.

4. The brain measurement apparatus according to claim 1, wherein each of the geomagnetic field nulling coil and the active shield coil is a pair of coils arranged with the multiple optically pumped magnetometers interposed therebetween.

5. The brain measurement apparatus according to claim 1, wherein the multiple optically pumped magnetometers are axial gradiometers having a measurement region and a reference region in a direction perpendicular to a measurement location and coaxially.

6. The brain measurement apparatus according to claim 1, wherein the multiple optically pumped magnetometers, the multiple magnetic sensors for geomagnetic field cancellation, the multiple magnetic sensors for active shield, and the receive coil are fixed to a non-magnetic frame above a measurement location.

7. The brain measurement apparatus according to claim 1, further comprising:
an electromagnetic shield for shielding high-frequency electromagnetic noise.

8. The brain measurement apparatus according to claim 1, wherein the multiple optically pumped magnetometers are configured to be applied a bias magnetic field so as to be sensitive to frequencies included in a range of 0 to 200 Hz, and
the another optically pumped magnetometer is configured to be applied a bias magnetic field so as to be sensitive to frequencies included in a range of 20 kHz to 500 kHz.

9. A brain measurement apparatus, comprising:
a magnetoencephalograph including multiple optically pumped magnetometers configured to measure a brain's magnetic field, multiple magnetic sensors for geomagnetic field cancellation configured to measure a magnetic field relevant to geomagnetic field at a position of each of the multiple optically pumped magnetometers, multiple magnetic sensors for active shield configured to measure a fluctuating magnetic field at the position of each of the multiple optically pumped magnetometers, a geomagnetic field nulling coil for cancelling the magnetic field relevant to the geomagnetic field, and an active shield coil for cancelling the fluctuating magnetic field;

an MRI apparatus including a static magnetic field coil for applying a static magnetic field, a gradient magnetic field coil for applying a gradient magnetic field, a transmission coil for transmitting a transmission pulse having a predetermined frequency, and a receive coil for detecting a nuclear magnetic resonance signal generated by the transmission of the transmission pulse;

a controller configured to, when measuring the brain's magnetic field, control a current to be supplied to the geomagnetic field nulling coil and a current to be supplied to the active shield coil based on measured values of the multiple magnetic sensors for geomagnetic field cancellation and measured values of the multiple magnetic sensors for active shield and, when measuring an MR image, control the static magnetic field and the gradient magnetic field by controlling currents to be supplied to the static magnetic field coil and the gradient magnetic field coil and generate an MR image based on an output of the receive coil, wherein the multiple optically pumped magnetometers, the multiple magnetic sensors for geomagnetic field cancellation, the multiple magnetic sensors for active shield, and the receive coil are fixed to a non-magnetic frame above a measurement location.

10. A brain measurement method using a magnetoencephalograph including multiple optically pumped magnetometers configured to measure a brain's magnetic field, multiple magnetic sensors for geomagnetic field cancellation configured to measure a magnetic field relevant to geomagnetic field at a position of each of the multiple optically pumped magnetometers, multiple magnetic sensors for active shield configured to measure a fluctuating magnetic field at the position of each of the multiple optically pumped magnetometers, a geomagnetic field nulling coil for cancelling the magnetic field relevant to the geomagnetic field, and an active shield coil for cancelling the fluctuating magnetic field, an MM apparatus including a static magnetic field coil for applying a static magnetic field, a gradient magnetic field coil for applying a gradient magnetic field, a transmission coil for transmitting a transmission pulse having a predetermined frequency, and a receive coil for detecting a nuclear magnetic resonance signal generated by the transmission of the transmission pulse, an output coil that is electrically connected to the receive coil and is configured to output a magnetic signal based on a current flowing through the receive coil, and another optically pumped magnetometer configured to detect the magnetic signal output by the output coil, the method comprising:

when measuring the brain's magnetic field, controlling a current to be supplied to the geomagnetic field nulling coil and a current to be supplied to the active shield coil based on measured values of the multiple magnetic sensors for geomagnetic field cancellation and measured values of the multiple magnetic sensors for active shield; and when measuring an MR image, controlling the static magnetic field and the gradient magnetic field by controlling currents to be supplied to the static magnetic field coil and the gradient magnetic field coil and generating an MR image based on an output of the receive coil, wherein the MR image is generated based on the magnetic signal detected by the another optically pumped magnetometer.

11. The brain measurement method according to claim 10, wherein the geomagnetic field nulling coil is formed by a geomagnetic field nulling coil for cancelling a magnetic field of the geomagnetic field and a gradient magnetic field nulling coil for cancelling a gradient magnetic field of the geomagnetic field.

* * * * *